US012600695B2

(12) United States Patent
Idowu et al.

(10) Patent No.: US 12,600,695 B2
(45) Date of Patent: Apr. 14, 2026

(54) METHOD FOR REACTIVATING A PRECIOUS METAL IRON CATALYST AND PERFORMING A CHEMICAL REACTION

(71) Applicant: Dow Global Technologies LLC, Midland, MI (US)

(72) Inventors: Ademola D. Idowu, Lake Jackson, TX (US); Brian Cramm, Lake Jackson, TX (US)

(73) Assignee: Dow Global Technologies LLC, Midland, MI (US)

( * ) Notice: Subject to any disclaimer, the term of this patent is extended or adjusted under 35 U.S.C. 154(b) by 304 days.

(21) Appl. No.: 17/787,795

(22) PCT Filed: Jan. 4, 2021

(86) PCT No.: PCT/US2021/012031
§ 371 (c)(1),
(2) Date: Jun. 21, 2022

(87) PCT Pub. No.: WO2021/141839
PCT Pub. Date: Jul. 15, 2021

(65) Prior Publication Data
US 2023/0025700 A1 Jan. 26, 2023

Related U.S. Application Data

(60) Provisional application No. 62/957,392, filed on Jan. 6, 2020.

(51) Int. Cl.
| | |
|---|---|
| *C07C 209/36* | (2006.01) |
| *B01J 23/89* | (2006.01) |
| *B01J 23/96* | (2006.01) |
| *B01J 38/48* | (2006.01) |
| *C07C 209/86* | (2006.01) |

(52) U.S. Cl.
CPC ......... *C07C 209/36* (2013.01); *B01J 23/8906* (2013.01); *B01J 23/96* (2013.01); *B01J 38/485* (2013.01); *C07C 209/86* (2013.01)

(58) Field of Classification Search
CPC .................................................. B01J 23/8906
USPC ................................. 502/338, 337, 325, 326
See application file for complete search history.

(56) References Cited

U.S. PATENT DOCUMENTS

| | | | | | |
|---|---|---|---|---|---|
| 2,823,235 | A | * | 2/1958 | Penrose ................ | C07C 209/36 546/171 |
| 2,857,337 | A | * | 10/1958 | Spiegler ................... | B01J 23/40 502/325 |
| 3,127,356 | A | * | 3/1964 | Hamilton, Jr. et al. . | B01J 23/00 502/185 |
| 3,558,514 | A | * | 1/1971 | Schutt ...................... | B01J 27/04 502/25 |
| 3,959,382 | A | * | 5/1976 | Yeh ........................ | C07C 45/006 502/25 |
| 4,999,326 | A | * | 3/1991 | Sikkenga ................. | B01J 38/52 502/29 |
| 5,143,872 | A | * | 9/1992 | Weiss ....................... | B01J 38/64 502/25 |
| 6,350,911 | B1 | * | 2/2002 | Sander ................. | B01J 19/2475 564/418 |
| 2002/0077504 | A1 | * | 6/2002 | Albers ................... | B01J 23/462 564/423 |

FOREIGN PATENT DOCUMENTS

| | | | | | |
|---|---|---|---|---|---|
| DE | 102011003590 | A1 | * | 9/2011 | .............. B01J 21/18 |
| EP | 2471768 | A1 | * | 7/2012 | ........... C07C 209/36 |
| EP | 1852392 | B | | 6/2013 | |

OTHER PUBLICATIONS

M. Králik, et al.. 6 Journal of Chemistry and Chemical Engineering 1074-1082 (2012) (Year: 2012).*
G. Alloncle et al., C.R. Chemi, 637-646 (2009) (Year: 2009).*
E. Auer et al., The Synthesis of Amines by Catalytic Hydrogenation of Nitro Compounds, in Catalysis of Organic Reactions, 293-300 (2000, M. Ford, Ed.) (Year: 2000).*
M. Argyle et al., 5 Catalyst, 145-269 (2015) (Year: 2015).*
W. Li et al., 8 RSC Advances, 35496-35502 (2018) (Year: 2018).*
P. Rodriguez et al., Applied Catalysis A: General, 66-72 (2012) (Year: 2012).*

* cited by examiner

*Primary Examiner* — Alexander R Pagano
(74) *Attorney, Agent, or Firm* — Warner Norcross + Judd LLP

(57) ABSTRACT

Catalytic activity of a spent precious metal-iron catalyst is restored by combining the spent catalyst with an iron (III) compound. This can be performed by adding the iron (III) compound into a chemical reaction that contains the spent precious metal-iron catalyst. It is unnecessary to add more of the precious metal. The process is especially useful in a continuous process for converting a nitro compound such as nitrobenzene to the corresponding amine.

5 Claims, No Drawings

METHOD FOR REACTIVATING A PRECIOUS METAL IRON CATALYST AND PERFORMING A CHEMICAL REACTION

This invention relates to methods for reactivating precious metal-iron catalysts and to chemical reactions that use a precious metal-iron catalyst.

Precious metal catalysts are used industrially in various types of chemical manufacturing processes. They are used, for example, to hydrogenate organic nitro compounds such as nitrobenzene to the corresponding amine; to hydrogenate organic aldehydes to the corresponding alcohols; to produce hydrogen peroxide via an anthraquinone process; as well as many others.

The precious metal catalysts sometimes contain iron, which in some cases enhances the performance of the catalyst. See, for example, U.S. Pat. No. 2,823,235, Underhill et al., *JohnsonMathey Technol. Rev.,* 2018, 62, (4) 417, Chin et al., *Applied Catalyst A: General* 302 (1) 2006 22-31, Kuroki et al., *ACS Appl. Energy Mater.* 2018, 1,2, 324-330, and He et al., *J. Hazardous Materials,* 164(1), 2009, 126-132.

These catalysts tend to deactivate over time, which results in a decline in reaction rate, particularly in continuous processes. This requires the catalyst to be replaced periodically. Replacing the catalyst involves considerable expense.

An alternative to replacing the catalyst is to reactivate it. Various methods for accomplishing this have been mentioned. U.S. Pat. No. 3,959,382 describes a process in which palladium hydrogenation catalysts are reactivated by treatment with alkali or alkaline earth metal compounds in a liquid medium. The process described in U.S. Pat. No. 4,999,326 involves a step of contacting the deactivated catalyst with a polar solvent for naphthalenic compounds. U.S. Pat. No. 5,143,872 and EP 1853292 describe contacting the spent catalyst with alkaline aqueous solutions. These methods have little or no effect when applied to precious metal-iron catalysts. Taninouchi et al., *Metallurgical and Materials Transaction B* 49(4) 2918 1781-1793 describe a method in which platinum group metals are recovered from spent automotive catalytic converters by treatment with $FeCl_2$ vapor at temperatures around 927° C. This forms an iron-precious metal alloy that is recoverable using magnetic means.

This invention is in one aspect a method for reactivating a spent precious metal-iron catalyst. The method comprises combining the spent precious metal-iron catalyst with an iron (III) compound while adding to the spent precious metal-iron catalyst no more than 10% by weight of the precious metal, based on the weight of the iron in the added iron (III) compound.

The applicant has unexpectedly found that the activity of a spent precious metal-iron catalyst can be at least partially restored by combining it with an iron (III) compound. The iron (III) compound is not an additional quantity of the precious metal-iron catalyst. To the contrary, little or none of the precious metal is combined with the spent catalyst in this method; the addition of the iron compound alone is sufficient to restore catalytic activity. Thus, it is unnecessary in this process to add more of the precious metal, whether in the form of the starting precious metal-iron catalyst or in any other form.

Another unexpected benefit is that no special processing steps are needed to obtain the desired increase in catalytic activity. It is sufficient simply to form a physical admixture of the spent precious-metal catalyst and the iron (III) compound. Accordingly, the iron (III) compound in some embodiments can be added directly into a chemical manufacturing operation in which the spent precious metal-iron catalyst is present, without any need to treat the spent catalyst separately or to alter process conditions in any way (other than by the addition of the iron (III) compound) to obtain an increase in catalytic activity.

Thus, in a second aspect the invention is a catalytic process for producing one or more chemical products, comprising a) performing a chemical reaction by subjecting, in the presence of a precious metal-iron catalyst, one or more starting compounds to reaction conditions at which the one or more starting compounds react to form the one or more chemical products, the reaction being continued for a period of time such that the precious metal-iron catalyst becomes at least partially spent;

b) thereafter adding an iron (III) compound one or more times to the reaction vessel while adding no more than 10% by weight of the precious metal, based on the weight of the iron in the added iron (III) compound, and thereafter continuing to perform the chemical reaction in the presence of the at least partially spent precious metal-iron catalyst and the added iron (III) compound.

The invention has particular significance to continuously operated hydrogenation processes for producing an aromatic amine. In a third aspect, the invention is such a process, comprising a) performing a continuous reduction reaction by continuously or intermittently introducing a starting nitroaromatic compound and hydrogen to a reaction vessel in the presence of a precious metal-iron catalyst and continuously or intermittently removing from the reaction vessel water and an aromatic amine produced by the reaction of the starting nitroaromatic compound and hydrogen, the reduction reaction being continued for a period of time such that the precious metal-iron catalyst becomes at least partially spent;

b) thereafter adding an iron (III) compound one or more times to the reaction vessel while adding no more than 10% by weight of the precious metal, based on the weight of the iron in the added iron (III) compound, and thereafter continuing to perform the continuous reduction reaction in the presence of the at least partially spent precious metal-iron catalyst and the iron (III) compound.

The precious metal-iron catalyst is a composition containing at least one precious metal and iron. By "precious metal" it is meant gold, silver, ruthenium, rhodium, palladium, osmium, iridium and platinum. Palladium and/or platinum are preferred among these.

The precious metal and iron in the catalyst may be present in metallic form, as an alloy with each other, or in the form of a salt, oxide or other compound. The precious metal and iron may be deposited together on a support. Such a support may be a fixed bed type of support or a particulate support. The support may be any material that is inert under the conditions of the reaction. Examples of useful support materials include zeolites, molecular sieves, titanium dioxide, alumina, silica, other metal oxides and/or nitrides, and various forms of carbon, including carbon black, activated carbon (including activated charcoal and activated coke), graphite, charcoal and the like. Activated carbon is a microporous carbon that has a porosity of at least 3000 $m^2/g$ as measured by gas adsorption methods.

A fresh supported catalyst may contain, for example, 1 to 25% by weight of the precious metal and 1 to 25% by weight of iron, based on the total weight of the supported catalyst, on a dry basis. In some embodiments, the weight of the precious metal and iron each constitute at least 2%, at least 3% or at least 4% of the total dry weight of the fresh supported catalyst, and up to 20%, up to 15%, up to 10% or up to 7.5% thereof. By "fresh" catalyst, it is meant one that has not been previously used.

In a particular embodiment, the catalyst is a carbon-supported palladium-iron or palladium-platinum-iron catalyst containing, when fresh, 2 to 10%, especially 3 to 7.5% by weight palladium and/or platinum and a like amount of iron, in each case based on the total dry weight of the fresh supported catalyst.

Methods of making precious metal-iron catalysts are described, for example, in U.S. Pat. No. 2,823,235, Berry et al., *Applied Catalysis A: General* 204(2) 2000 191-201, Underhill et al., *JohnsonMathey Technol. Rev.,* 2018, 62, (4) 417, He et al., *J. Hazardous Materials,* 164(1), 2009, 126-132, Chin et al., *Applied catalyst A: General* 302 (1) 2006 22-31, and Kuroki et al., *ACS Appl. Energy Mater.* 2018, 1,2, 324-330. Catalysts made in accordance with any of these methods are suitable for use the invention.

The precious metal-iron catalyst is used to perform a chemical reaction. In the chemical reaction, one or more starting compounds are subjected to reaction conditions, including the presence of the catalyst, at which the one or more starting compounds react to form one or more chemical products.

The chemical reaction may be, for example, an oxidation reaction, such as the oxidation of phenol to form hydrogen peroxide or the oxidation of carbon monoxide; a dechlorination or dehydrochlorination reaction; a hydrodeoxygenation reaction; a reduction reaction; a hydrogenation reaction; or any other reaction for which the precious metal-iron catalyst is useful.

In some embodiments the chemical reaction is a reduction (hydrogenation) of a nitro compound to the corresponding amine. The nitro compound may be a nitroaromatic compound in which the nitro group or groups are bonded directly to a carbon atom of an aromatic ring. In a particular embodiment, the nitro compound is nitrobenzene and the amine produced is aniline.

The chemical reaction is performed in the presence of the precious metal-iron catalyst for a period of time such that the precious metal-iron catalyst has become at least partially spent. The catalyst is considered to be at least partially spent when, during or after its use in the chemical reaction, it exhibits a decline in activity as indicated by a resulting decline in a rate of the chemical reaction in the presence of the precious metal-iron catalyst by itself (i.e., without added iron (III) compound). The decline in activity may be measured in situ by measuring the reaction rate periodically, or by recovering all or a portion of the catalyst and measuring its activity according to a suitable test.

Applicants have found that the metals in the catalyst, particularly the iron, can become depleted during use. The metal content, and the iron content in particular, of the catalyst therefore changes during use from that of the fresh catalyst. The change in metal content, and in particular the depletion of iron, is believed to at least partially cause the decline in catalyst activity and resultant decline in the reaction rate. Thus, the catalyst is considered to be at least partially spent if it has lost all or a portion of its starting iron content (i.e., its iron content before being placed into use).

In this invention, iron is replenished by combining the at least partially spent precious metal-iron catalyst with an iron (III) compound. This is done while adding no more than 10% by weight of the precious metal to the spent precious metal-iron catalyst, based on the weight of the iron in the added iron (III) compound. Preferably, any precious metal added during this combination step is added in at most impurity levels in the iron (III) compound, such as no more than 500 ppm, no more than 100 ppm or no more than 10 ppm by weight based on the weight of the iron. In some embodiments, no precious metal is added with the iron (III) compound, such that the entire quantity of precious metal in the combination is provided by the spent precious metal-iron compound.

Additional precious metal, if added at all, may be added in the form of fresh precious metal-iron catalyst.

The iron (III) compound may be, for example, an iron (III) halide such as iron (III) fluoride, iron (III) chloride, iron (III) bromide and the like; iron (III) nitrate, iron (III) phosphate; iron (III) pyrophosphate, iron oxide ($Fe_2O_3$); basic iron (III) carbonate, iron (III) carbonate, ferric hydroxide, an iron (III) alkoxide; an iron (III) aryloxide such as iron phenoxide; an iron (III) carboxylate; iron (III) salicylate; iron (III) 3,5-di-t-butyl salicylate; iron (III) acetylacetonate; and iron (III) t-butylacetylacetonate. Inorganic iron (III) compounds are preferred in some instances to avoid introducing extraneous organic species into the reaction.

The iron (III) compound in some embodiments is a solid under the conditions of the chemical reaction in which it is employed and may be insoluble in and, except for its catalytic activity, non-reactive in the reaction mixture. A solid and/or supported iron (III) compound may be in the physical form of, for example, a catalyst bed or particles. If in particulate form, a solid and/or supported iron (III) compound (including support if any) may have a longest dimension of 10 nm to 10 mm or 25 nm to 100 μm.

The iron (III) compound may be carried on a support such as is described above with respect to the precious metal-iron catalyst.

A particularly suitable iron (III) compound, especially for reduction and/or hydrogenation reactions such as the reduction of an organic nitro compound to the corresponding amine (in particular the hydrogenation of a nitroaromatic compound such as nitrobenzene to an aromatic amine such as aniline), is ferric hydroxide or iron oxide, which may be carried on an inorganic support, in particular a carbon support (such as an activated carbon support) as described above.

The spent precious metal-iron catalyst and iron (III) compound can be combined by simple mixing of the materials to form a physical admixture. It is generally unnecessary to treat the physical admixture in any particular way to, for example, promote or cause a chemical reaction, fuse, alloy or otherwise marry the starting materials. The physical admixture has been found to be catalytically active, often as much so as fresh precious metal-iron catalyst.

The mixing can be performed, for example, by recovering all or a portion of at least partially spent precious metal-iron catalyst from the chemical reaction and combining the recovered precious metal-iron catalyst with the iron (III) compound to form the physical admixture. The physical admixture thus obtained can be reintroduced into the chemical reaction of interest. By "recovering", it is meant the catalyst is at least partially separated from the reactants of the chemical reaction. This can be done, for example, by removing the spent catalyst from the reaction vessel, by removing the reactants from the reaction vessel and leaving the spent catalyst in the reaction vessel, or by withdrawing from the reaction vessel a recycle stream that contains all or a part of the catalyst. Recycling spent catalyst, such as by forming an admixture of iron (III) compound and spent catalyst recovered from the reaction vessel and re-introducing the resulting admixture to the reaction vessel, is not considered as adding precious metal for purposes of this invention.

An unexpected advantage of the invention is that the spent catalyst does not need to be recovered from the chemical reaction. It can be combined with the iron (III) compound in the presence of the reactants, even as the chemical reaction proceeds, forming the mixture of spent catalyst and iron (III) compound in situ. In such embodiments, the iron (III) compound can simply be introduced to the reaction vessel as the reaction is proceeding in the presence of the spent catalyst, the chemical reaction thereafter being performed in the presence of both the spent catalyst and the iron (III) compound.

In general, the mixture of at least partially spent precious metal-iron catalyst and iron (III) compound is introduced to the chemical reaction when the starting precious metal-iron catalyst has become at least partially spent. The decline in catalytic activity and resultant decline in reaction rate can be monitored if desired, using any suitable analytical method as appropriate for the particular chemical reaction. For example, the conversion of one or more of the starting materials can be determined, with lower conversions indicating a loss of catalytic activity and a decline in reaction rate. Similarly, the rate of consumption of one or more of the starting materials can be measured, a drop in the consumption rate again indicating declines in catalytic activity and reaction rate. The concentration and/or rate of production of one or more products of the chemical reactions can be measured as indicia of a decline in catalytic activity and reaction rate. If desired, samples of the precious metal-iron catalyst can be recovered from the chemical reaction and analyzed for iron content or evaluated for its catalytic activity.

Instead of or in addition to monitoring the chemical reaction, a general rate of decline in catalytic activity may be established empirically for any particular chemical reaction under a particular set of operating conditions. The empirical data is then used to estimate one or more times at which the catalytic activity and reaction rate will have declined and the iron (III) compound should be provided to the reaction vessel. The empirical data can be used in this manner to establish a schedule for providing the iron (III) compound into the reaction. The iron (III) compound in such cases can be added intermittently or continuously to maintain a desired catalytic activity and reaction rate.

The chemical reaction thereafter is continued in the presence of both the spent precious metal-iron catalyst and the iron (III) compound.

The invention is useful in a continuous process. In such a continuous process one or more starting materials are continuously or intermittently introduced to a reaction vessel in the presence of the precious metal-iron catalyst, and one or more reaction products are continuously or intermittently removed from the reaction vessel. The iron (III) compound is continuously or intermittently added to the reaction vessel during the continuous operation as the precious metal-iron catalyst becomes partially or entirely spent, thereby increasing the catalytic activity and rate of the chemical reaction. The chemical reaction is thereafter continued in the presence of the partially or entirely spent precious metal-iron catalyst and the iron (III) compound.

In a particular embodiment, the chemical reaction is a reaction of a starting nitroaromatic compound with hydrogen to produce the corresponding aromatic amine. In the case in which the nitroaromatic compound is nitrobenzene, the amine product will be aniline.

In a useful continuous process for producing aniline in accordance with the invention, nitrobenzene and hydrogen are intermittently or continuously introduced to a lower section of a reaction vessel that is operated at a temperature above the boiling temperature (at one atmosphere pressure) of aniline, such as 200 to 260° C. The pressure within the reaction vessel may be, for example 10 to 30 atmospheres (1013-3040 kPa) gauge. The nitrobenzene and hydrogen react in the presence of the precious metal-iron catalyst in the reaction vessel to produce aniline and water. Aniline and water are continuously or intermittently removed in the gas phase from an upper portion of the reaction vessel and taken for purification of the aniline. The reaction is continued for a period of time until which the precious metal-iron catalyst is at least partially spent. The iron (III) compound is added to the reaction vessel intermittently or periodically during the continuous operation, and the reaction is continued in the reaction vessel after the addition of the iron (III) compound, in the presence of the at least partially spent precious metal-iron catalyst and the iron (III) compound.

In a continuous process, a convenient way of manner of adding the iron (III) compound is to withdraw a recycle stream containing spent precious metal-iron catalyst from the reaction vessel, combining the spent precious metal-iron catalyst with the iron (III) compound in all or a portion of recycle stream, and then reintroducing that portion of the recycle stream containing the spent precious metal-iron catalyst and added iron (III) compound into the reaction vessel. This can be performed intermittently or continuously. The recycle stream typically contains a liquid phase that may include, for example, unreacted starting materials, solvent and/or some quantity of the product. Some or all of the liquid phase may be removed from the recycle stream before it is reintroduced into the reaction vessel. For example, product may be recovered from the recycle stream before the stream is reintroduced into the reaction vessel. In the case of a nitroaromatic hydrogenation reaction, the recycle stream may contain some quantity of the product aromatic amine (aniline in the case of a nitrobenzene hydrogenation). Some or all of the aromatic amine may be recovered from the recycle stream before it is reintroduced into the reaction vessel.

The following examples are provided to illustrate the invention but are not intended to limit the scope thereof. All parts and percentages are by weight unless otherwise indicated. All molecular weights are number averages unless otherwise indicated.

EXAMPLES 1-4 AND COMPARATIVE SAMPLES A AND B

Reaction time experiments are performed in the following general manner: A 300 mL autoclave (Autoclave Engineers Model ABA-300, steam-jacketed and equipped with an agitator) is charged with 0.027 to 0.028 gram of a palladium-iron catalyst as described below, 17.2 mL of nitrobenzene, 30 mL methanol and 50 mL water. The reactor is sealed, purged with hydrogen, and then pressurized with nitrogen to 30 bars (3040 kPa) gauge pressure. The reactor contents are heated to 100° C. by flowing steam into the jacket. The time at which the reactor contents reach 100° C. is designated time $T_0$. The pressure in the reactor is measured continuously. The point in time at which the pressure becomes constant ($T_c$, indicating the completion of the reaction) is determined. The reaction time is calculated as $T_c-T_0$.

For Comparative Sample A, the palladium-iron catalyst is a fresh catalyst sample containing about 4.6% by weight palladium, 0.4% by weight platinum and 5.15% by weight iron (all by induction-coupled plasma-mass spectroscopy (ICP-MS) on a dry weight basis). The metals are carried on carbonaceous support particles. The palladium-iron catalyst is made according to a method such as is described in U.S. Pat. No. 2,823,235.

For Comparative Sample B, the palladium-iron catalyst is a spent sample of the same palladium-iron catalyst, obtained from a commercial aniline production plant.

The reaction times for Comparative Samples A and B are 7.1 to 7.2 minutes and 19.3-19.7 minutes. The spent catalyst therefore has approximately one-third the activity of the fresh catalyst on this test.

ICP-MS analysis of the spent catalyst reveals that the palladium and platinum levels in the spent catalyst are virtually unchanged from those of the fresh catalyst. However, the iron content of the spent catalyst is found to be reduced by about 60%, to about 2.1% by weight of the catalyst.

Comparative Sample B is repeated 4 additional times, in each case adding ferric chloride ($FeCl_3 \cdot 6H_2O$) as a physical admixture with the spent catalyst. In Example 1 enough of the ferric chloride is added to provide 1 part iron per 100 parts by weight of the spent catalyst. In Examples 2-4, ferric chloride is added to provide, 2, 3 and 4 parts iron per 100 parts of the spent catalyst. The approximate total amount of iron (including that from the spent catalyst and ferric chloride) and reaction time are as indicated in Table 1, together with the results from Comparative Samples A and B.

TABLE 1

| Designation | Catalyst Description | Approximate Iron content %[1] | Reaction Time, minutes |
|---|---|---|---|
| A* | Fresh Catalyst | 5.15 | 7.1-7.2 |
| B* | Spent Catalyst | 2.1 | 19.3-19.7 |
| 1 | Spent Catalyst + Ferric Chloride | 3.1 | 16.0-16.4 |
| 2 | Spent Catalyst + Ferric Chloride | 4.1 | 12.8-12.9 |
| 3 | Spent Catalyst + Ferric Chloride | 5.1 | 7.6-7.9 |
| 4 | Spent Catalyst + Ferric Chloride | 6.1 | 6.8-7.1 |

*Not an example of the invention.
[1]By weight of the palladium-iron catalyst (spent or fresh).

As the data in Table 1 shows, adding ferric chloride into the reaction reduces the reaction time very significantly compared to the spent catalyst. When the iron content in the reaction mixture is increased to approximately that of the fresh catalyst, the reaction time becomes essentially the same if not faster than that provided by the fresh catalyst. Smaller amounts of the added iron (III) compound provide a lesser but significant benefit.

EXAMPLE 5 AND COMPARATIVE SAMPLE C

Although greatly improved reaction rates are obtained by adding ferric chloride into the nitrobenzene reduction reaction described in the earlier examples, the presence of chloride ion causes unwanted by-products to form in that particular reaction. Therefore, an iron (III) compound that contains few if any halide ions is preferred for reducing nitro compounds to the corresponding amine.

Ferric chloride and activated carbon are combined in the presence of water at a weight ratio of iron to carbon of 1:20. Sodium bicarbonate is added, which reacts with ferric chloride to produce basic ferric carbonate, which is precipitated onto the activated carbon, and sodium chloride. The iron carbonate-activated carbon particles are separated from the liquid phase and heated to 80° C. for 30 minutes to decompose the iron carbonate to ferric hydroxide. The particles are then washed, filtered and dried.

Comparative Sample C is performed according to the general reaction time procedure described above. The catalyst is a spent palladium-iron catalyst from a commercial aniline production facility, originally made according to a method as described in U.S. Pat. No. 2,823,235.

In Example 5, a mixture of the same spent catalyst and the ferric hydroxide-activated carbon particles is used. The mixture is formed by adding the spent catalyst and ferric hydroxide-activated carbon particles separately to the reactor. Enough of the ferric hydroxide-activated carbon particles are added to provide about 4 wt-% iron, based on the weight of the spent catalyst particles. The total iron content in the spent catalyst and ferric hydroxide-activated carbon particles combined is 5-6.25% of the weight of the spent catalyst particles. Results are as indicated in Table 2, together with those of Comparative Sample A.

TABLE 2

| Designation | Catalyst | Approximate Iron content, %[1] | Reaction Time, minutes |
|---|---|---|---|
| A* | Fresh Catalyst | 5.15 | 7.1-7.2 |
| C* | Spent Catalyst | 2-2.2 | 19.8-21.7 |
| 5 | Spent Catalyst + Iron Hydroxide-Activated Carbon Particles | 5-6.25 | 7.1-7.5 |

*Not an example of the invention.
[1]By weight of the palladium-iron catalyst (spent or fresh).

As the data in Table 2 demonstrates, adding iron in the form of iron hydroxide supported on activated carbon restores the catalytic activity to approximately that of the fresh catalyst. No unwanted by-products of the reaction form.

What is claimed is:

1. A process for producing an aromatic amine, comprising
a) performing a continuous reduction reaction by continuously or intermittently introducing a starting nitroaromatic compound and hydrogen to a reaction vessel in the presence of a precious metal-iron catalyst supported on a carbonaceous support wherein the precious metal is palladium, platinum or a mixture of palladium and platinum and continuously or intermittently removing from the reaction vessel water and an aromatic amine produced by the reaction of the starting nitroaromatic compound and hydrogen, the reduction reaction being continued for a period of time such that the precious metal-iron catalyst becomes at least partially spent;
b) thereafter adding an iron (III) compound one or more times to the reaction vessel while adding no more than 10% by weight of the precious metal, based on the weight of the iron in the added iron (III) compound wherein the iron (III) compound added is not supported and physically independent from the no more than 10% by weight of the precious metal, and thereafter continuing to perform the continuous reduction reaction in the presence of the at least partially spent precious metal-iron catalyst and the iron (III) compound.

2. The process of claim 1 wherein the iron (III) compound is an iron (III) halide, iron oxide, basic iron (III) carbonate, iron (III) carbonate, or iron (III) hydroxide.

3. The process of claim 1 wherein the carbonaceous support comprises activated carbon having a porosity of at least 3000 $m^2/g$ as measured by gas adsorption methods.

4. The process of claim 1 wherein the precious metal-iron catalyst is a carbon-supported palladium-iron or palladium-platinum-iron catalyst containing, when fresh, 3 to 7.5% by weight palladium and/or platinum and a like amount of iron, in each case based on the total dry weight of the fresh supported catalyst.

5. The process of claim 1 wherein:

the precious metal-iron catalyst is a palladium iron catalyst;

the iron (III) compound is ferric chloride or ferric hydroxide; and/or the iron (III) compound is added in an amount sufficient to provide 1 to 4 parts by weight of the spent palladium iron catalyst.

* * * * *